United States Patent [19]

Zinnanti

[11] Patent Number: 5,451,380
[45] Date of Patent: Sep. 19, 1995

[54] LAPAROSCOPIC INSTRUMENT TRAY SYSTEM

[76] Inventor: William J. Zinnanti, 3815 Northland, Newbury Park, Calif. 91320

[21] Appl. No.: 231,519

[22] Filed: Apr. 22, 1994

[51] Int. Cl.⁶ ............................................. A61L 2/26
[52] U.S. Cl. .................................. 422/300; 206/370
[58] Field of Search ............. 206/370, 369, 364, 63.5; 422/292, 300

[56] References Cited

U.S. PATENT DOCUMENTS

| | | | |
|---|---|---|---|
| 4,577,755 | 3/1986 | Ramsay | 206/370 |
| 4,865,821 | 9/1989 | Langdon | 422/300 |
| 5,193,672 | 3/1993 | Long | 422/300 X |
| 5,215,726 | 6/1993 | Kudla et al. | 206/370 X |
| 5,279,800 | 1/1994 | Berry, Jr. | 422/300 |
| 5,294,413 | 3/1994 | Riihimaki et al. | 422/297 |

Primary Examiner—Robert J. Warden
Assistant Examiner—E. Leigh Dawson
Attorney, Agent, or Firm—Allen A. Dicke, Jr.

[57] ABSTRACT

The laparoscopic instrument tray system comprises an instrument tray suitable for holding laparoscopic instruments for storage and sterilization and suitable for holding the instruments in an accessible position for use. The tray comprises sides with upwardly and downwardly directed notched cross bars which receive the shanks of laparoscopic instruments. Bails hold the instruments in place during sterilization and transport and are raised to permit access. The instrument tray has a bottom (preferably perforated) for holding other types of instruments for sterilization and access.

14 Claims, 4 Drawing Sheets

LAPAROSCOPIC INSTRUMENT TRAY SYSTEM

FIELD OF THE INVENTION

This invention is directed to a laparoscopic instrument tray system which receives and retains the laparoscopic instruments through storage, sterilization and use. In use, it presents the laparoscopic instruments for convenient access.

BACKGROUND OF THE INVENTION

Surgical instruments used in the operating room are conventionally placed in a basket and sterilized. From the basket, they are placed on a tray close to the operating field. Various instruments are delivered to the surgeon as required by the procedure.

The disadvantages of the present system include the handling of the instruments between sterilization and their individual delivery to the surgeon. Additionally, when the instruments are large, such as laparoscopic instruments, they take up considerable tray space so that the number of instruments immediately accessible is limited. A more convenient system for the handling of surgical instruments, particularly laparoscopic instruments, is required.

SUMMARY OF THE INVENTION

In order to aid in the understanding of this invention, it can be stated in essentially summary form that it is directed to a laparoscopic instrument tray system which includes an instrument tray with sides. Notched cross bars extend between the sides above the floor of the tray. The notches receive the cannula of laparoscopic instruments. The space within the tray below the instruments can be used for instruments and aides to surgery.

It is, thus, a purpose and advantage of this invention to provide a laparoscopic instrument tray system which includes structure which positions the laparoscopic instruments in the tray with the handles hanging down next to each other so that a plurality of such instruments can be arranged next to each other and spaced from each other to provide high packing density without overlapping of the instruments to permit individual accessibility of the instruments.

It is another purpose and advantage of this invention to provide a laparoscopic instrument tray system which has sufficient space therein below the rack of laparoscopic instruments to receive other surgical devices which might be employed in the same surgical procedure, such as scopes, adaptors, cables, trocars, and sleeves so that all of the equipment and instruments required for a procedure can be assembled, sterilized and conveniently positioned for use.

It is a further purpose and advantage of this invention to provide an instrument tray system which receives different types of laparoscopic instruments and holds them in position during assembly, sterilization, transportation and storage and which makes them available during a surgical procedure.

It is a further purpose and advantage of this invention to provide a laparoscopic instrument tray system which is convenient and easy to use so that the desired laparoscopic instruments are readily accessible and to provide a system which is economic and reliable so that it may be widely utilized.

Other purposes and advantages of this invention will become apparent from a study of the following portion of the specification, the claims and the attached drawings.

DESCRIPTION OF THE PREFERRED EMBODIMENT

Figure 1:
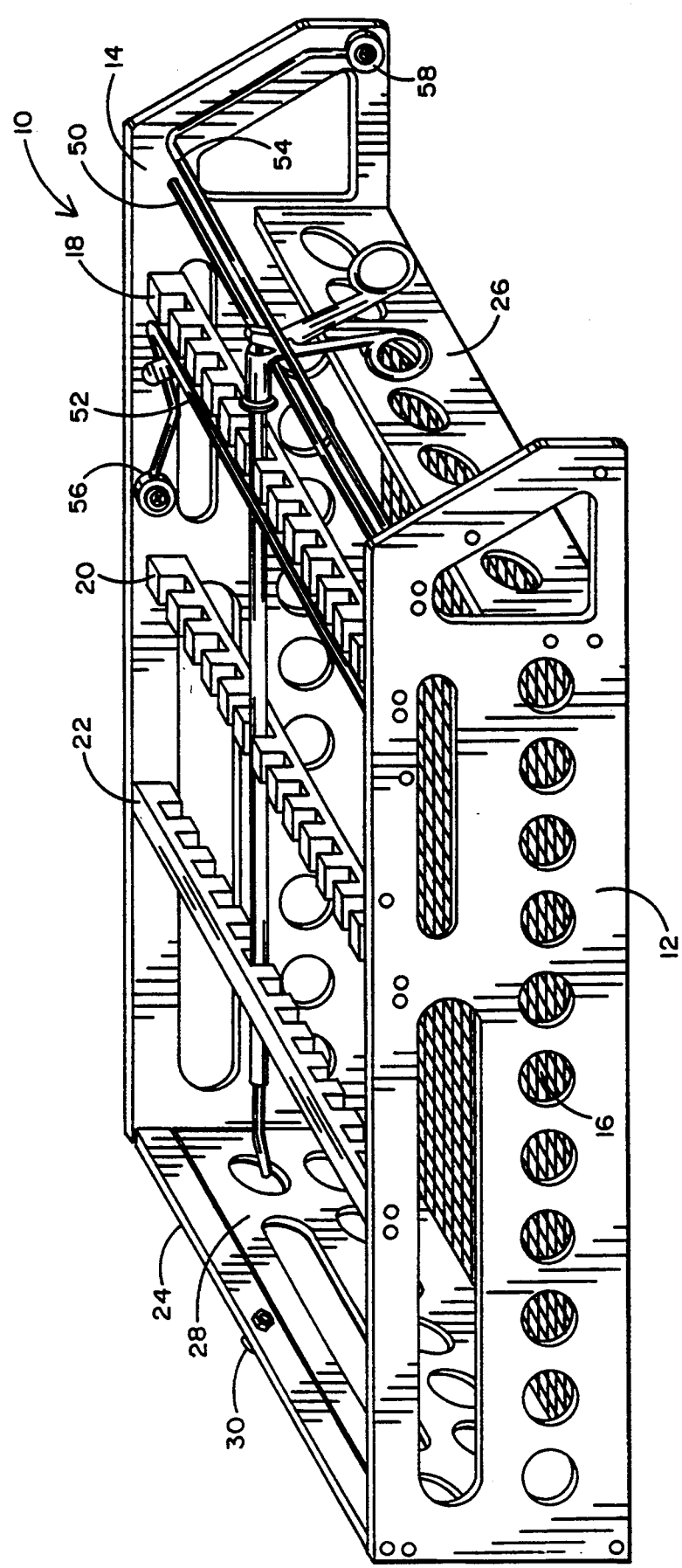
FIG. 1 is an isometric view of the laparoscopic instrument tray with a laparoscopic instrument retained therein.
Figure 2:
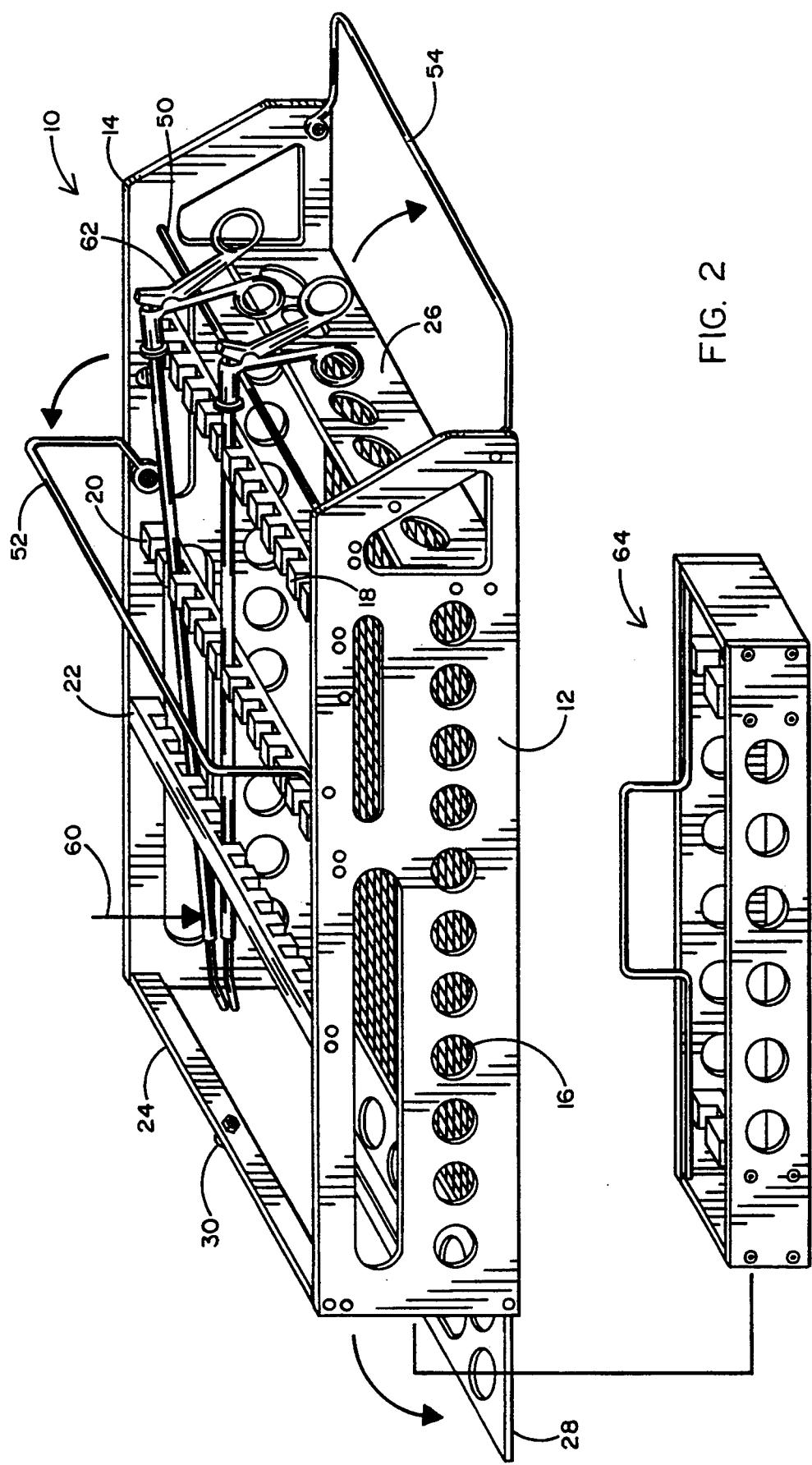
FIG. 2 is similar to FIG. 1, but showing the balls released to free the laparoscopic instrument in the tray and with the holder removed from the floor of the tray.

The laparoscopic instrument tray system of this invention is generally indicated at 10 in FIGS. 1 and 2. The laproscopic instrument tray has sides 12 and 14 which are preferably perforated for lightness as well as for free circulation of sterilizing gas. Tray bottom 16, seen through the perforations in the near side, is a mesh or perforated bottom to also provide for free gas circulation. Front, intermediate and rear cross bars 18, 20 and 22 are secured adjacent the top edge of the sides between the sides and are secured to the sides. Back cross bar 24 is also secured between the sides at the very back of the tray. In addition, front door 26 is secured between the sides and pivots with respect thereto to open the front of the tray. Back door 28 is similarly pivoted between the sides and is shown in the closed position in FIG. 1. In FIG. 2, back door 28 is shown in the open position. Latch 30 is configured to releasably hold the back door in its raised position.

Figure 5:
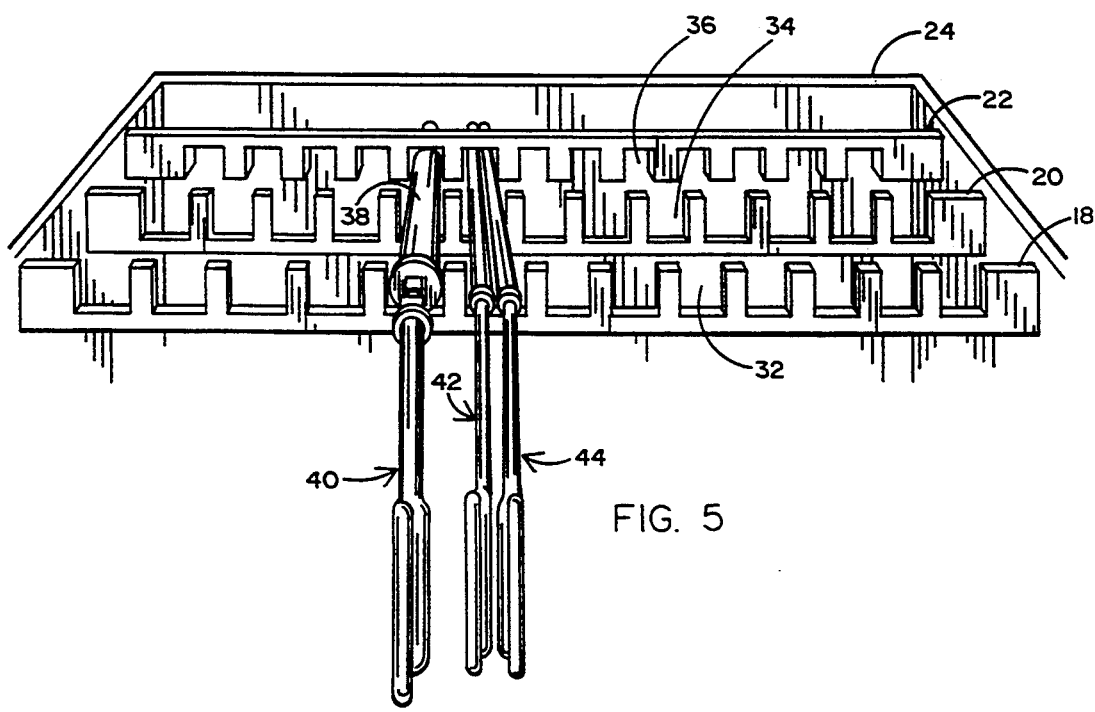
FIG. 5 is an end view of the tray, with parts broken away, showing the handle end of the laparoscopic instruments.

Each of the cross bars 18, 20 and 22 has notches therein. The notches in cross bars 18 and 20 are upwardly directed, while the notches in cross bar 22 are downwardly directed. There is the same number of notches in each of the cross bars, and the notches are in alignment from one cross bar to the next from front to back, as is seen in FIG. 5. This alignment of the notches permits laparoscopic instruments to be placed therein. As is best seen in FIGS. 1 and 2, laparoscopic instruments are placed in the top of the open top notches in bars 18 and 20 and beneath the rear cross bar 22 into an aligned notch. For identification, aligned notches 32, 34 and 36 are seen in FIG. 5. The notches are preferably slightly over 10 millimeters in width to freely receive a cannula of 10 millimeter diameter. A 10 millimeter diameter cannula 38 is shown on laparoscopic instrument 40. Similar laparoscopic instruments are fitted with 5 millimeter cannulas, and for instruments of that size, two can be fitted into one set of aligned notches in the cross bars. Laparoscopic instruments 42 and 44 lie together in a single set of notches, as shown in FIG. 5.

Figure 3:
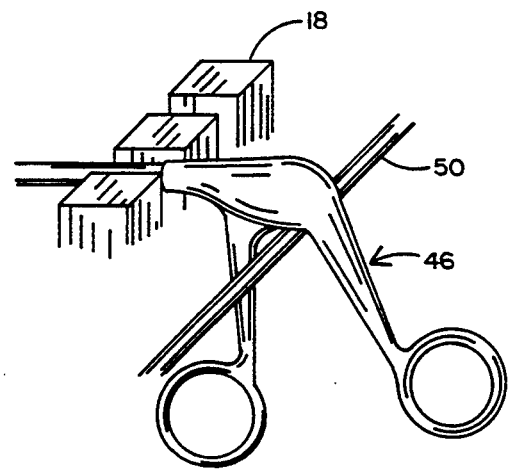
FIG. 3 is an enlarged isometric view, with parts broken away, showing one type of laparoscopic instrument positioned in the tray.
Figure 4:
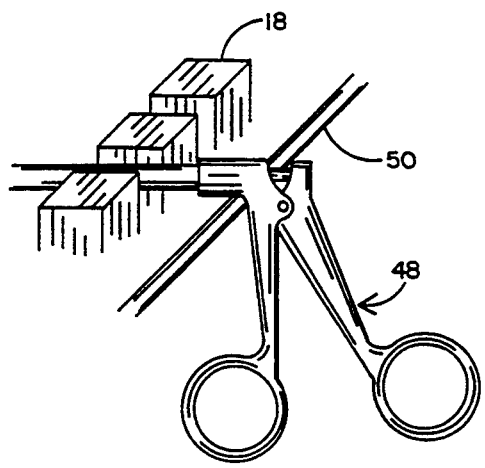
FIG. 4 is an enlarged isometric view, with parts broken away, showing another type of laparoscopic instrument positioned within the tray.

FIGS. 3 and 4 show laparoscopic instruments 46 and 48 which are of different handle configurations. Cross rod 50 extends between the sides 12 and 14 toward the front of the tray 10. As seen in FIGS. 1 and 2, cross rod 50 lies halfway between the front cross bar 18 and the front of the tray. The cross rod 50 is positioned to be engaged by the different styles of laparoscopic instruments 46 and 48. This indicates that several different styles of laparoscopic instruments may be positioned within and retained within the tray 10.

After the desired selection of laparoscopic instruments is positioned in the tray, each with its cannula engaged in a set of aligned notches in the cross bars, the instruments are retained therein by means of bails 52 and 54, which are seen in the closed position in FIG. 1 and in the open position in FIG. 2. Each of the bails is a formed wire with an elongated center section and a loop at each end. The center section is substantially straight and substantially the length of the distance between the sides 12 and 14. The loops on the end lie on the inside of the sides. Loop 56 is seen on bail 52, and loop 58 is seen on bail 54. There are similar loops on the near ends of the bails. These loops lie against the inside of the sides and are rotatably secured thereto by means of machine screws and washers. The bails act to retain the laparoscopic instruments in place when they are lying in their notches in the cross bars, when the bails are in their retaining position. This is the position shown in FIG. 1. In this position, the instrument tray can be moved without fear of the laparoscopic instruments being dropped from the tray.

When access is desired to the laparoscopic instruments and when the tray is adjacent the surgeon at the operating field, the bails are open to the position shown in FIG. 2. In this position, the laparoscopic instruments can be readily removed by the scrub nurse or by the surgeon. As is seen in FIG. 5, the handles of the laparoscopic instruments may lie close to each other. In order to conveniently retrieve a selected one of the laparoscopic instruments, the forward end may be pressed down with the finger, as indicated by arrow 60 in FIG. 1. This raises the handle 62 of that laparoscopic instrument so that it is separated from the other handles and conveniently grasped.

FIGS. 3 and 4 show laparoscopic instruments 46 and 48 of different configurations. Most laparoscopic instruments will fit in the top rack by resting across the cross rod 50, as shown by laparoscopic instrument 48 in FIG. 4. Special patterns, such as Stryker and Access will need to straddle the cross bar in the manner shown by laparoscopic instrument 46 in FIG. 3.

The cross bars are thus suitable for receiving selected laparoscopic instruments, such as are sorted out for the next day's operation. When so positioned, the bails are brought down, the tray is delivered for sterilization and later positioned in the operating room. However, a number of other surgical instruments and devices may be necessary for the same operation. In order to keep them together, such can be placed on the tray bottom 16 during the sorting, sterilizing and delivering steps. However, it is also convenient to provide a holder 64 to store and hold during the various steps such additional items as camera and scope, as well as other loose instruments, adaptors and cables. The holder is sized to receive other surgical instruments and other surgical needs. It can be placed into the tray through door 28 and retained therein during sterilization and storage. This possibility of assembling all of the needs for a particular operation into the tray at a prior time, such as the night before, permits several sets of instruments to be prepared and sterilized. This pre-assembling function can save up to 20 minutes of operating room time to set up for a surgery.

Figure 6:
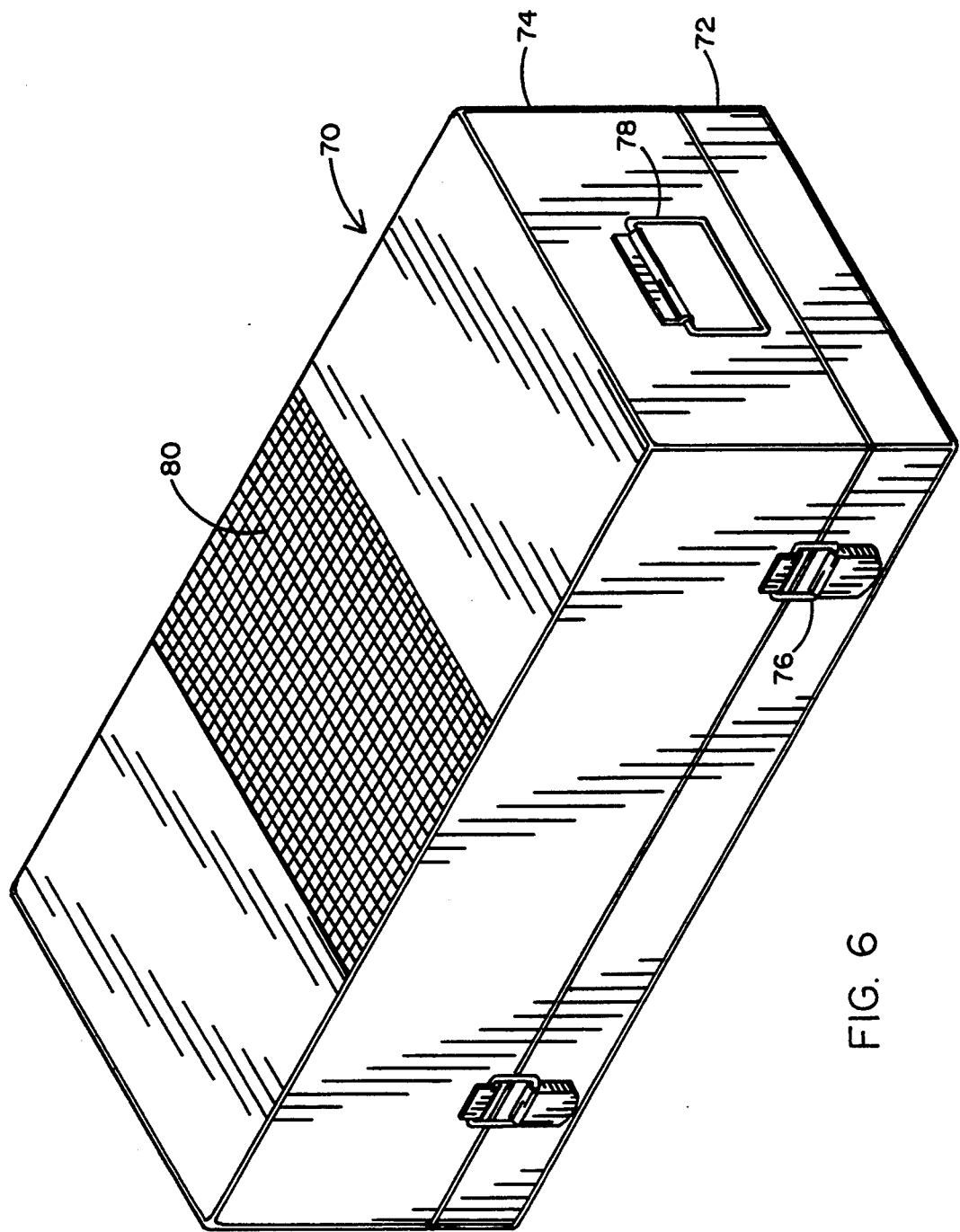
FIG. 6 is an isometric view of the laparoscopic instrument tray system of this invention enclosed in a case.

Case 70, shown in FIG. 6, is configured to receive the laparoscopic instrument tray 10, as shown in FIG. 1. In this configuration, the tray contains laparoscopic instruments and has its bails positioned to lock the laparoscopic instruments in place. The case 70 comprises a base 72 and a cover 74, which cooperate together to enclose the tray. The base is latched onto the cover by means of a plurality of latches, one of which is seen at 76. The case has handles at each end with the handle 78 shown at the near end. Both the base and cover have openings therein, such as screen 80, to permit the contents to be gas-sterilized. Once the laparoscopic instrument tray is loaded with surgical instruments, it is placed in the case 70, and the case is placed in the gas sterilizer. After sterilization, it may be stored in a sterile environment and is ultimately delivered to the operating room. The case is opened, and the laparoscopic instrument tray 10 carrying the sterile surgical instruments is removed from the case and placed where needed in the operating room.

This invention has been described in its presently contemplated best embodiment, and it is clear that it is susceptible to numerous modifications, modes and embodiments within the ability of those skilled in the art and without the exercise of the inventive faculty. Accordingly, the scope of this invention is defined by the scope of the following claims.

What is claimed is:

1. A laparoscopic instrument tray system comprising:
    first and second tray sides spaced from each other, said tray sides each having a lower edge and being at least as long as the length of a laparoscopic instrument to be stored therein;
    means connected to both said first and second sides for retaining said first and second sides in a position where they are spaced from each other;
    first and second cross bars extending at least a portion of the space between said sides, both said first and second cross bars having notches therein, said first cross bar being positioned in said tray with its notches directed upwardly and said second cross bar being positioned in said tray with its notches directed downwardly, said notches in said cross bars being sized to receive the cannula of a laparoscopic instrument, said first cross bar being sufficiently high so that the handle of the laparoscopic instrument engaged in a notch therein is above said lower edges of said sides so that a laparoscopic instrument can be engaged in a notch under said second cross bar and over said first cross bar to releasably retain a laparoscopic instrument in said tray with its handle above the lower edge of said tray sides.

2. The laparoscopic instrument tray system of claim 1 wherein there is a third cross bar, said third cross bar having upwardly directed notches and being positioned between said first and second cross bars, said notches in said first, second and third bars being in line so that a laparoscopic instrument may be engaged in said notches of all three of said bars and said third cross bar extends all the way between said first and second sides.

3. The laparoscopic instrument tray system of claim 1 wherein each of said cross bars extends all the way between said first and second sides and each of said cross bars is attached to both said first and said second sides.

4. The laparoscopic instrument tray system of claim 1 wherein there is a bail movably attached to said tray, said bail being positioned on the side of said first cross bar remote from said second cross bar, said bail being movable from a first position where it is away from a laparoscopic instrument lying over said first cross bar and under said second cross bar to a second locking position to retain a laparoscopic instrument in said notches in said first and second cross bars.

5. A laparoscopic instrument tray comprising:
first and second spaced sides, said first and second spaced sides each having a length longer and a height higher than the length and height of a laparoscopic instrument to be positioned in said tray;
a bottom attached to both said first and second sides for holding said first and second sides in spaced position;
at least first and second cross bars spaced above said bottom, each attached to both of said first and second sides, said first cross bar having upwardly open spaced notches therein, said second cross bar having downwardly open spaced notches therein, said spaced notches being of sufficient size to accept the cannula of a laparoscopic instrument so that the tip end of a laparoscopic instrument can be engaged over said first cross bar and under said second cross bar and engaged in a notch in each said cross bar to releasably retain a laparoscopic instrument in said tray with its handle spaced from the bottom of said tray, said cross bars being positioned so that the tip end of the laparoscopic instrument can be depressed toward said bottom of said tray to raise the handle end of the laparoscopic instrument to permit accessibility thereto.

6. The laparoscopic instrument tray of claim 5 wherein said tray has a bail being positioned on the side of said first bar remote from said second bar, said bail being movable from a first position where it is away from a laparoscopic instrument lying over said first cross bar and under said second cross bar to a second locking position to retain a laparoscopic instrument in said notches in said first and second cross bars.

7. The laparoscopic instrument tray of claim 5 wherein there are first, second and third cross bars, said third cross bar being positioned between said first and second cross bars and said third cross bar has upwardly directed notches in line with said notches in said first and second cross bars in a direction parallel to said first and second sides.

8. The laparoscopic instrument tray system of claim 7 wherein a movable bail is attached to said first and second sides, said bail having a first, retaining position wherein said bail engages on a laparoscopic instrument, said bail having a second, free position wherein said bail does not inhibit the raising of the handle end of the laparoscopic instrument resting on said cross bars.

9. The laparoscopic instrument tray of claim 8 wherein said bail is a first bail and there is in addition a second bail, said second bail being movable to a position where it engages on the handle of the laparoscopic instrument in said tray.

10. The laparoscopic instrument tray of claim 5 wherein said tray further includes an instrument holder, said instrument holder being sized and said cross bars being sufficiently above said tray bottom that said holder can be inserted into said tray below said cross bars.

11. The laparoscopic instrument tray system of claim 10 wherein said tray includes a movable back door so that said back door can be opened for insertion of said holder and closed to retain said holder in said tray.

12. The laparoscopic instrument tray of claim 11 further including a case, said case having a base and a cover, said base and said cover being sized to receive therein said laparoscopic instrument tray and releasably retain said tray.

13. The laparoscopic instrument tray of claim 12 wherein both said base and said cover of said case are perforated to permit sterilization of the contents of said case.

14. The laparoscopic instrument tray of claim 5 further including a case, said case having a base and a cover, said base and said cover being sized to receive therein said laparoscopic instrument tray and releasably retain said tray.

* * * * *